United States Patent
Uber, III

Patent Number: 5,920,054
Date of Patent: Jul. 6, 1999

[54] CLOSED LOOP INFORMATION PATH FOR MEDICAL FLUID DELIVERY SYSTEMS

[75] Inventor: Arthur E. Uber, III, Pittsburgh, Pa.

[73] Assignee: Medrad, Inc., Indianola, Pa.

[21] Appl. No.: 08/949,327

[22] Filed: Oct. 3, 1997

Related U.S. Application Data

[63] Continuation of application No. 08/729,098, Oct. 11, 1996, Pat. No. 5,739,508, which is a continuation of application No. 08/273,665, Jul. 12, 1994, abandoned.

[51] Int. Cl.⁶ .................................................. G06K 17/00
[52] U.S. Cl. .......................... 235/375; 235/383; 235/384
[58] Field of Search .................................. 235/375, 383, 235/384

[56] References Cited

U.S. PATENT DOCUMENTS

| | | |
|---|---|---|
| 3,349,713 | 10/1967 | Fassbender . |
| 3,523,523 | 8/1970 | Reich . |
| 3,701,345 | 10/1972 | Heilman . |
| 3,755,655 | 8/1973 | Sewecal . |
| 3,793,600 | 2/1974 | Groubard . |
| 3,812,843 | 5/1974 | Wjutten . |
| 3,895,220 | 7/1975 | Nelson . |
| 3,898,983 | 8/1975 | Elam . |
| 3,941,126 | 3/1976 | Dietrich . |
| 3,958,103 | 5/1976 | Oka . |
| 3,968,195 | 7/1976 | Bishop . |
| 3,995,381 | 12/1976 | Manfred . |
| 4,001,549 | 1/1977 | Corwin . |
| 4,038,981 | 8/1977 | LeFevre . |
| 4,151,845 | 5/1979 | Clemens . |
| 4,187,057 | 2/1980 | Xanthopoulos . |
| 4,199,000 | 4/1980 | Edstrom . |
| 4,207,871 | 6/1980 | Jenkins . |
| 4,223,675 | 9/1980 | Williams . |
| 4,262,824 | 4/1981 | Hrynewycz . |
| 4,280,494 | 7/1981 | Cosgrove . |
| 4,319,568 | 3/1982 | Tregouing . |
| 4,340,153 | 7/1982 | Spivey . |
| 4,341,153 | 7/1982 | Bowser . |
| 4,392,849 | 7/1983 | Petre . |
| 4,396,385 | 8/1983 | Kelly . |
| 4,434,822 | 3/1984 | Bellany . |
| 4,447,230 | 5/1984 | Gula . |
| 4,479,760 | 10/1984 | Bilstad . |
| 4,479,761 | 10/1984 | Bilstad . |
| 4,479,762 | 10/1984 | Bilstad . |
| 4,544,949 | 10/1985 | Kurihara . |
| 4,551,133 | 11/1985 | Zegers . |
| 4,559,036 | 12/1985 | Wunsch . |

(List continued on next page.)

FOREIGN PATENT DOCUMENTS

| | | |
|---|---|---|
| 2045070 | 2/1992 | Canada . |
| 0337924 | 10/1989 | European Pat. Off. . |
| 0343501 | 11/1989 | European Pat. Off. . |
| 0600448 | 6/1994 | European Pat. Off. . |
| 0650739 | 5/1995 | European Pat. Off. . |
| 2561949 | 10/1985 | France . |
| 4121568 | 10/1992 | Germany . |
| 2207749 | 2/1989 | United Kingdom . |
| 2252656 | 8/1992 | United Kingdom . |
| WO/01754 | 9/1980 | WIPO . |
| WO85/00292 | 1/1985 | WIPO . |
| WO94/15664 | 7/1994 | WIPO . |

*Primary Examiner*—Harold Pitts
*Attorney, Agent, or Firm*—Pillsbury Madison & Sutro LLP

[57] ABSTRACT

This invention relates generally to the field of medical devices for delivering medicinal fluids to patients during medical procedures and more particularly, this invention relates to improved medical fluid delivery systems and methods of use which incorporate a closed loop information path from the manufacturer to a product user such as a hospital or other medical institution and back to the original manufacturer. The information originally incorporated with the product is used by the consumer to aid in use of the product. The information which accompanies the product is updated and new information is added in order to provide the manufacturer with information on how the product is used.

8 Claims, 1 Drawing Sheet

U.S. PATENT DOCUMENTS

| | | |
|---|---|---|
| 4,563,175 | 1/1986 | LaFond . |
| 4,585,009 | 4/1986 | Barker . |
| 4,610,670 | 9/1986 | Spencer . |
| 4,610,790 | 9/1986 | Reti . |
| 4,634,426 | 1/1987 | Kamen . |
| 4,636,144 | 1/1987 | Abe . |
| 4,682,170 | 7/1987 | Kubata . |
| 4,710,166 | 12/1987 | Thompson . |
| 4,750,643 | 6/1988 | Wertrich . |
| 4,754,786 | 7/1988 | Roberts . |
| 4,783,273 | 11/1988 | Knutsson . |
| 4,798,590 | 1/1989 | O'Leary . |
| 4,835,521 | 5/1989 | Andrejasich . |
| 4,840,620 | 6/1989 | Kobayashi . |
| 4,853,521 | 8/1989 | Claeys . |
| 4,854,324 | 8/1989 | Hirschman . |
| 4,857,056 | 8/1989 | Talonn . |
| 4,879,880 | 11/1989 | Harrison . |
| 4,880,014 | 11/1989 | Zarowitz . |
| 4,887,208 | 12/1989 | Schneider . |
| 4,887,554 | 12/1989 | Whitford . |
| 4,925,444 | 5/1990 | Orkin . |
| 4,929,818 | 5/1990 | Bradbury . |
| 4,943,279 | 7/1990 | Samiotes . |
| 4,946,439 | 8/1990 | Eggers . |
| 4,949,256 | 8/1990 | Humble . |
| 4,950,245 | 8/1990 | Brown . |
| 4,978,335 | 12/1990 | Arthur . |
| 4,981,467 | 1/1991 | Bobo . |
| 5,059,173 | 10/1991 | Sacco . |
| 5,078,683 | 1/1992 | Sancoff . |
| 5,100,380 | 3/1992 | Epstein . |
| 5,199,604 | 4/1993 | Palmer . |
| 5,207,642 | 5/1993 | Orkin . |
| 5,230,614 | 7/1993 | Zanger . |
| 5,273,537 | 12/1993 | Haskvitz . |
| 5,274,218 | 12/1993 | Urata . |
| 5,310,997 | 5/1994 | Roach . |
| 5,317,506 | 5/1994 | Coutre . |
| 5,328,463 | 7/1994 | Barton . |
| 5,339,799 | 8/1994 | Kami . |
| 5,349,625 | 9/1994 | Born . |
| 5,354,273 | 10/1994 | Hagen . |
| 5,361,761 | 11/1994 | Vanlysel . |
| 5,362,948 | 11/1994 | Morimoto . |
| 5,450,847 | 9/1995 | Kampfe . |
| 5,458,128 | 10/1995 | Polanyi . |
| 5,485,831 | 1/1996 | Holdsworth . |
| B1 5,009,654 | 4/1991 | Minshall . |

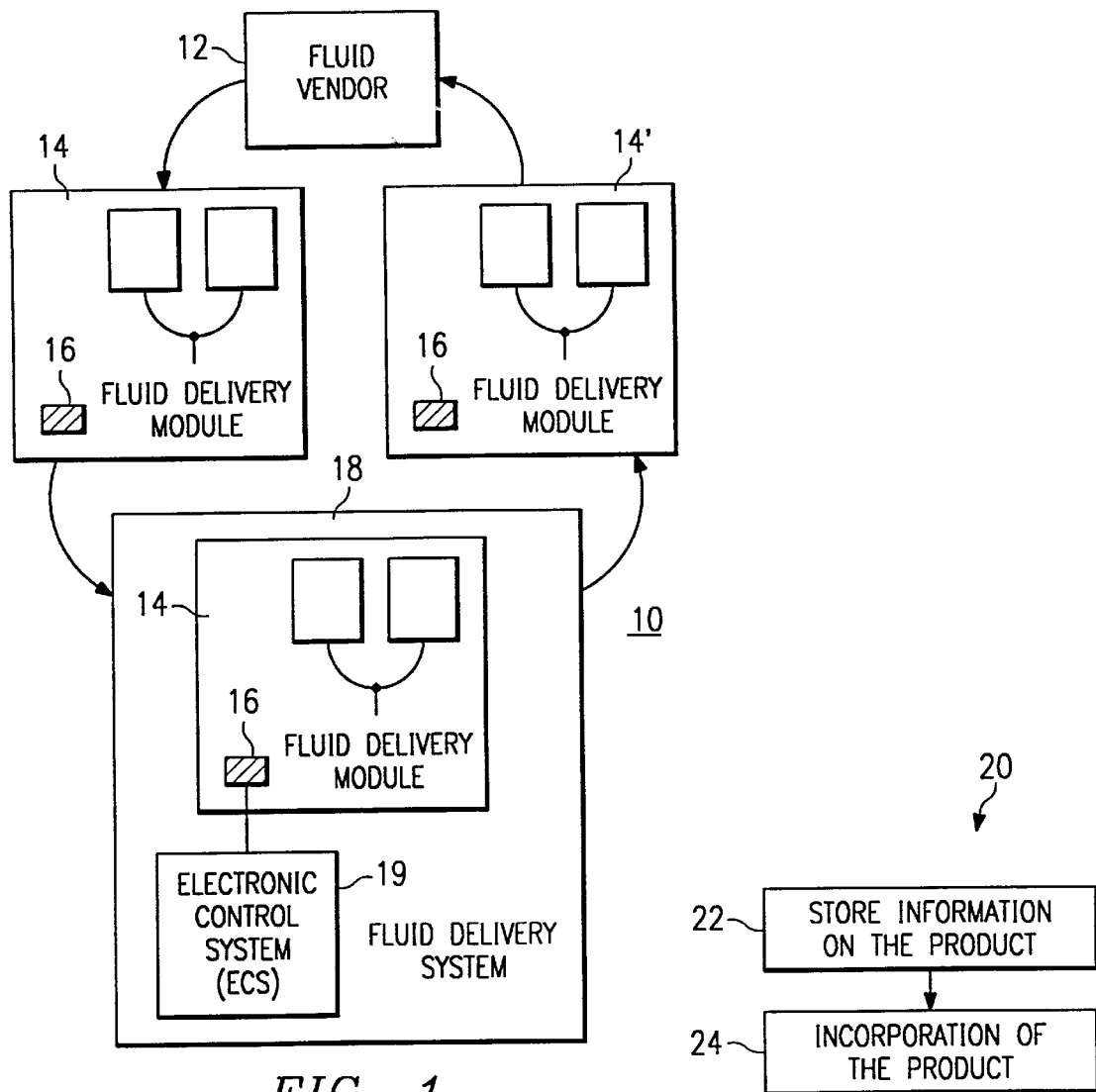

CLOSED LOOP INFORMATION PATH FOR MEDICAL FLUID DELIVERY SYSTEMS

This is a continuation of application Ser. No. 08/729,098, filed Oct. 11, 1996 now 5,739,508 which is a continuation of U.S. application Ser. No. 08/273,665, filed Jul. 12, 1994, abandoned.

This invention relates generally to the field of medical devices for delivering medicinal fluids to patients during medical diagnostic procedures and more particularly, this invention relates to improved medical fluid delivery systems and methods of use which incorporate a closed loop information path from the vendor to a product user such as a hospital or other medical institution and back to the original vendor or its representative. The information originally incorporated with the product is used by the consumer to aid in use of the product. The information which accompanies the product is updated and new information is added in order to provide the vendor with information on how the product is used.

DESCRIPTION OF THE RELATED ART

It has been recognized that the inclusion of machine readable identification codes on a product can increase the utility, reliability and efficiency of the product by allowing the product to be more readily and accurately incorporated into a system which uses the product. The inclusion of these codes primarily eliminates the potential for introducing operator error by removing the need for the system operator to enter various product information which alters operation of the system. Additionally, these systems save time by reducing or eliminating the time it takes for the information to be entered into the system. These systems are extremely useful in the medical field where accuracy is critical and failure to properly use a system can have devastating or even fatal consequences.

Conventional medical fluid delivery systems have not used machine readable codes beyond bar codes used for inventory information, primarily because the systems of the prior art were not sufficiently versatile to make such systems useful. Conventional medical fluid delivery systems generally used a single disposable source of contrast media. In these systems, a doctor would select a concentration of contrast media and injection rate based primarily on the study to be done, with consideration of the size and weight of the patient as well as other additional factors. This fixed set of injection parameters is considered to be a standard delivery protocol. Once the doctor selected these parameters, the entire bottle of contrast media was used for that patient. There simply was no need for these systems to read and react to information relating to the contents of the fluid container because the entire container was completely injected or discarded, and the systems did not operate differently for different types and concentrations of contrast media.

Although it has been recognized that varied dosing requirements for patients exist in medical imaging procedures, conventional medical imaging procedures continue to use pre-set doses or standard protocols for injecting contrast media during medical imaging procedures. Standard protocols have been used primarily to minimize the potential for errors and decrease the likelihood of having to repeat the procedure, an occurrence which requires that the patient be exposed to additional radiation and contrast media. As noted, in prior art contrast delivery systems, once a bottle of contrast media was opened for use on a patient it could not be used on another patient primarily due to contamination considerations. Existing contrast delivery systems do not prevent the source of contrast media used for an injection from being contaminated with body fluids of the patient.

Some of the shortcomings of existing imaging systems and procedures have been addressed and resolved in co-pending application Ser. No. 08/144,462 filed October 1993, titled "Total System For Contrast Delivery," and U.S. Ser. No. 08/309,820, titled "Patient Specific Dosing Contrast Delivery Systems and Methods," filed Sep. 21, 1994 (Attorney Docket No. 46169-185). Each application is incorporated herein by reference.

These applications disclose a contrast media delivery system which provides a source of contrast media which is sufficiently isolated from a patient undergoing an imaging procedure that the source of contrast media may be used on additional patients without concern for contamination. The system incorporates a source of contrast media, and, if desired, a diluent. Each is sufficiently isolated from the patient to prevent contamination. The contrast preferably has a concentration which is the highest that would be used in an injection procedure so that the operator may combine the contrast media with a diluent and select the desired concentration of contrast media for any given procedure.

These improvements in the field of medical imaging systems present the need for a system which incorporates the ability to automatically read information from a source of contrast media which identifies at the very least, the amount and concentration of the source of contrast media. This is necessary so that the system may automatically adjust the mixture of contrast media and diluent for a desired concentration of contrast media. Furthermore, because the systems disclosed in the above-referenced co-pending applications are designed for use with more than one patient, the system must also be aware of the initial volume of fluid so that the system is able to automatically warn the operator when the supply of fluid is less than the amount necessary to complete a given imaging procedure. There is also a need to incorporate other useful information such as, for example expiration date of the material and information related to calibration of the device etc.

A fluid delivery system which incorporates the use of machine readable codes associated with a fluid container used in the system would be much more useful and versatile if the system was also capable of updating the codes or adding additional information to the record member which contains the original codes. The updated information could be used during future procedures, such as, for example, by noting the amount of contrast media which has previously been used from a given source so that the system may warn an operator when there is insufficient fluid to complete a given procedure. New information could also be added to the record member which is useful for the original vendor such as information relating to how the system is actually used. Such information could also be used for billing of the customer, the patient, or for determining royalty payments. This is especially useful in systems which are reused or recycled because these devices are already returned to the vendor where this information could readily be extracted. Alternatively, the information could be electronically transmitted to the vendor if the fluid containers are not returned.

Accordingly, it is an object of the present invention to provide an improved fluid delivery system which incorporates the use of machine readable codes on the fluid containers for the system to read and use for calculating injection parameters.

It is a further object of the present invention to provide a fluid delivery system which is capable of updating and adding new information to the machine readable codes used by the system.

It is another object of the present invention to provide a closed loop information path which sends information from the manufacturer to a product user and back to the manufacturer or its representative using electronic transmission or machine writable/readable codes.

Numerous other objects and advantages of the present invention will become apparent from the following summary, drawings and detailed description of the invention and its preferred embodiment.

SUMMARY OF THE INVENTION

The invention includes apparatus and methods for storing machine readable and writable/readable codes on a record member which accompanies a medical fluid container for use in diagnostic medical imaging procedures or other medical fluid delivery systems. In a preferred embodiment, a medical fluid container is disclosed which contains machine readable codes located in a record member or memory device which accompanies the medical fluid container. The memory unit or record member, if electronic, incorporates its own power supply, if needed, so that its operation is independent from the system and information stored on the device will not be lost when the container is removed from the fluid delivery system.

The memory device in a preferred embodiment is partially encoded by the manufacturer although this is not necessary if information from the vendor is not required for system operation. An example of this would be when a vendor is only interested in determining the amount of fluid returned from a product user. In this situation, when the fluid container is returned to the vendor, the memory would contain information on the amount of fluid used so that the vendor could credit the consumer for the unused portion of the material.

In other interactive systems, the information typically encoded by the manufacturer would include information defining the amount of fluid in the container as well as the type and concentration of the fluid. When the fluid container of the present invention is attached to a medical fluid delivery system, the memory device is also connected to the system. The electronic control system (ECS) is able to read and download information into the system memory of the injection system. Disable circuitry is also incorporated into the fluid delivery system to prevent the fluid delivery system from operating without the proper connection of the memory device.

Other information is also incorporated by the vendor for use by the system such as the size of the fluid path elements which form the connection between the fluid containers and the patient. This is useful during calibration of the machine. Additionally, pressure rating of the fluid path could be incorporated to prevent the system from exceeding these limits inadvertently. This capability makes the system more flexible because it is able to use various components beyond those considered by the original designers. For example, tubing size information could be utilized for automated tubing filling to remove air from the lines after installation of the fluid path but before connection to a patient.

The memory device disclosed in the preferred embodiment is a writable/readable unit which incorporates its own independent power supply for sustaining information entered into its memory. Alternatively, it is contemplated that the system would employ an encoded magnetic strip which could also be updated. The system is therefore particularly useful in systems which are returned to a vendor for reuse or recycling. The system is able to provide a simple and economical means for the vendor to receive information on the use of its product. The control system automatically stores information related to the consumer's use of the system in the chip or chips which make up the memory unit or alternatively, the magnetic memory may be updated.

The memory unit would act as a "flight recorder" for the system and would store information related to the number of patients served by the fluid container, the actual concentration of contrast media used by the system and the flow rate of the injection etc. This information would enable manufacturers to improve service by providing them with up to date knowledge about actual use of their systems.

Other devices are disclosed which employ various types of read only encoding to increase the utility and efficiency of multi-patient contrast media injection systems as well as other medical fluid delivery systems. These systems primarily rely on the use of read only codes to supply information to the system which eliminates the potential for operator error while speeding up the procedure. These read only codes are typically bar codes or metal codes such as those used on film containers. Other interchangeable alternatives include optically sensed codes which are sensed via a CCD or equivalent device or physical surface codes detected by mechanical switches.

It is contemplated that the systems which rely on a read only device for the transfer of information also incorporate the ability to update the initial information or provide new information such as, for example, by printing new bar codes or otherwise altering the initial information.

Specific examples of these contemplated alternative designs are primarily directed to calibration of medical fluid delivery systems where it is necessary to receive information related to various operational parameters such as tubing size and pressure limits for safe operation of these systems. Incorporation of machine readable codes would enable the system to automatically calibrate, set pressure limits or verify whether correct parts are connected to the machinery. These systems may employ bar coding so that the operator may automatically input various operational parameters into the system via a bar code reader. The system would then perform various calculations to assure safe operation.

The bar codes may be found in association with the various parts of the system which form the fluid flow path so that the system is able to operate with a wide variety of these devices thereby increasing the overall versatility of the fluid delivery system.

BRIEF DESCRIPTION OF THE DRAWINGS

FIG. 1 is an illustration of a medical fluid delivery system which incorporates the present invention.

FIG. 2 is a flow diagram outlining use of the closed loop information path.

DESCRIPTION OF THE INVENTION AND ITS PREFERRED EMBODIMENT

FIG. 1 illustrates various stages of a system shown generally at 10 which incorporates the memory device of the present invention. The preferred embodiment incorporates a writable/readable memory device which is capable of sending and receiving information from a medical fluid delivery system. There are various memory devices which can be used in such a system, such as, for example, the DS14941-5f manufactured by Dallas Semiconductor of Dallas, Tex., or the Datakey manufactured by Datakey of Burnsville, Minn.

These chips can be packaged in a 16 mm Micro Can or incorporated into an insertable key-like device. The Dallas Semiconductor device incorporates its own power supply so that the contents of the memory will be sustained without an external supply of power. These devices have greater than 10 years of built in power which is more than sufficient for use with the present invention.

In the example of the preferred embodiment, a medical fluid vendor 12, produces a coded fluid delivery module 14 with an associated coded memory unit 16. The fluid delivery module 14 is a unit which incorporates various fluid delivery elements such as the fluid container or containers and associated tubing for making various connections to the fluid delivery system. These are preferably pre-connected and sterilized, but may also come as separate pieces which an operator must connect. The memory unit 16, which is considered to be associated with the various fluid delivery elements when it is associated with the fluid delivery module 14, may also be individually associated with one or with several of the fluid delivery elements.

The medical fluid vendor encodes information necessary for proper operation of a medical fluid delivery system 18. The fluid delivery system 18 incorporates the fluid delivery module 14 as shown in FIG. 1. Information is encoded and incorporated with the delivery module when the vendor packages the medical fluid delivery module for distribution. This information includes data related to the type, concentration and volume of the fluid in the container which accompanies the memory device. Other information which may be stored by the fluid vendor includes information related to calibration of the system such as the inside diameter, length and total volume of the tubing which accompanies the fluid delivery module to form the connection between the container and the injection system. Inside diameter is important if the tubing is part of a peristaltic pump. The inside diameter determines the calibration of the pump in milliliters/revolution. Inside diameter and length or total volume are used if the system will automatically purge air from the tubing. Information related to such variables as tubing pressure rating, expiration date of the material from which the tubing is made, or expiration date of the medical fluid may also be encoded. Certain memory locations would contain a system enable code to verify proper installation and reading of the coded fluid delivery module.

Information which is encoded and stored on the memory device is thus able to set operating parameters for the system. Operating parameters for the system include any data which is used in association with the operation of the system such as, for example, the calibration data and set up data noted above as well as data related to fluid characteristics such as type, concentration, manufacturer, expiration date and volume of fluid in the fluid container.

When a system operator installs the coded fluid delivery module 14 to the medical fluid delivery system 18 an electrical connection is made between the memory device and the fluid delivery system. With the Dallas device, the can may be mounted on the side of a fluid delivery module and spring contacts on the durable part of the delivery system would be contacted when the fluid path is properly in place. Alternatively, the Data key device could be attached to the fluid delivery module or any of its associated elements such as, for example, the fluid container, tubing or packaging by a lanyard. It would then be inserted into a socket on the durable equipment by the operator.

The Electronic Control System (ECS) 19 of the fluid delivery system communicates with the memory device 16 and downloads that information stored by the vendor which is necessary for use by the ECS in controlling the fluid delivery system. The ECS 19 controls the various elements of the fluid delivery system, such as the metering pumps, the pressurizing pump and heaters. These elements and others are described in more detail in the aforementioned co-pending applications.

In alternative embodiments which employ read only coding, such as, for example, bar codes, metal codes, optical sensing, mechanical codes, or patterned magnetic ink, the coding also includes enable codes to assure the proper reading of the coded information. The metal codes employ the use of decipherable current and resistance paths to transfer the coded information such as those used in cameras. The optical sensing capability refers to the use of CCD's to decipher coded information.

Once the fluid delivery system 18 receives the coded information, the system parameters are adjusted accordingly. The automatic reading of this information saves time and reduces the chances for operator error by eliminating the need for the operator to enter this system information.

Regardless of the embodiment, a successful read of the information enables the system for use during a given medical procedure. Any information necessary for instituting the injection is now contained in the memory of the of the ECS.

In a preferred embodiment, the fluid delivery system 18 may update the coded memory unit 16 either during and/or after completion of the medical procedure. This is accomplished by writing information to the coded memory unit 16. Totally new information may be added and existing information may be removed and updated. When using an electronic device, it is useful to read after writing to verify proper writing. The used fluid delivery module 14' is then returned to the vendor for information extraction and reuse or recycling.

In devices which incorporate read only type memory units the information may be updated by generating new codes, such as, for example, including a system which can generate and print new bar codes base on system generated information. The newly printed bar code is then placed on the unit which is returned to the vendor. It will be appreciated that it is not necessary for the vendor to include initial information in the coded device and that the coded device may be used for the return of information only. Alternatively, information may be received by the system only and not updated for return to the vendor. This is particularly true of calibration or set-up information for medical fluid delivery systems.

Set-up information refers generally to information which is used to set pressure limits and identify the total volume of the fluid delivery path. Calibration data refers generally to information used to set parameters for use of a pumping mechanism such as, for example, a peristaltic pump. Preparation of the fluid delivery system for use includes using the calibration and/or set-up data to set various system operating parameters.

In FIG. 2, the numeral 20 identifies a flow diagram according to the present invention. Information is stored in a memory unit which accompanies a product at a vendor site in initial step 22. The product is then delivered to a consumer which incorporates the product into a larger system at step 24. The stored information is used by the system in step 26 and new information relating to use of the product is then stored in step 28. The product is returned to the vendor in step 30 where the information relating to use of the product is received by the vendor. The system is particularly useful with reusable/recyclable products which in many instances are already returned to the vendor.

If the products do not need to be recycled, the information could be recovered by the vendor via electronic means, such as telephone or radio. This would be especially useful if billing is based upon this information. This is an alternate closed loop information path although a portion of the path relies on electronic transmission.

While the telephone or radio link is quick, it does require additional hardware cost. For very expensive machines, such as high end copiers by Xerox, telephone reporting is presently done. An advantage of the preferred embodiment of returning the information with the fluid path module is that no significant additional hardware is needed. The hardware needed to read the information from the electronic record member is sufficient to write to it.

Information is recovered periodically or shortly after a container is replaced. The recovered information includes some of the information the vendor initially stored with the fluid container as well as any new information added at the consumer site. Some of the recovered information, if desired, specifically identifies the particular fluid delivery module or memory unit by a unique serial number or reference code. The Dallas Semiconductor device has a portion of its memory dedicated for this purpose. The recovered information is useful in product tracking and potentially automatic re-ordering, to save customer time and reduce inventory costs. The recovered information may be tailored to individual vendor needs to assist in marketing efforts and increasing vendor knowledge about the use of their products. A wide variety of information could be stored and retrieved in this manner. The following table provides examples of information which would be stored and retrieved by the system:

Sample Table of Information

Per Fluid Module or Container:

A) Timestamp (Date and Time) of installation into the fluid delivery system.

B) Timestamp of removal from the system.

C) Number of injections.

D) Machine Identification Code.

E) Information on machine status.

F) Error codes, if any.

G) Contrast remaining, if any.

Per Usage

1) Timestamp of injection.

2) Concentration used, if able to dilute.

3) Total volume.

4) Flowrates and durations.

if patient specific information is used, then:

5) Procedure information.

6) Patient information (not identifying the patient)

Sample Uses for Information (A) and (B) can be combined with information on shipping time to a user to determine how many containers should be kept in inventory to meet demand but minimize the amount of inventory.

(C) and (D) accumulated by the vendor over time can help the vendor's service people determine when to perform preventative maintenance.

(E) and (F) can be used by the service people as well.

(A) compared with the expiration date can be used to make recommendations on inventory amounts or rotation procedure.

(G) compared to initial fill can be used if the billing of the customer is done on a per fluid volume basis rather than fixed price, or if there is a rebate for fluid returned unused.

The equipment could be provided on a lease basis, with the returned information (C) being used for customer billing.

(A), (B), (C) and the per injection information can be provided to the local salesman who may recommend that a different container size be used; smaller if (B)–(A) is near the limit for sterility time in the machine; larger is (B)–(A) is so short that the hassle of installing new containers is significant.

If a variable number of disposables come preattached, (C) can be used to recommend to the customer that he should have more or less disposable sets attached. More sets could save him money because he could use all the fluid more often. Fewer sets would save a little by having less to throw away.

The salesman can also use the per injection information to help one user achieve additional savings by sharing information about how other users use the system, such as protocols for various procedures.

The combined information of (A), (B) and (C) from many sites can be used for the vendor's production planning and strategic planning. This helps a vendor not be fooled by buying patterns which are influenced by year-end budgets, because the vendor has actual usage information.

Although the present invention has been described in terms of preferred embodiments, the present description is given by way of example only and is not intended to be limiting to the scope of the invention described and claimed herein.

I claim:

1. A method for using a consumable medical product including storing information on and retrieving information from a record member in association with the consumable medical product comprising the steps of:

a) storing information relative to the consumable medical product on the record member at a vendor site;

b) retrieving the stored information at a consumer site;

c) calculating parameters for operation of a system which incorporates the consumable medical product based on the retrieved information;

d) storing new information relating to using the consumable medical product on the record member at the consumer site; and e) retrieving the new information at the vendor site.

2. The method for using a consumable medical product of claim 1, further comprising the step of providing a readable/writable electronic device as the record member.

3. The method for using a consumable medical product according to claim 2, wherein a magnetic strip is provided as the record member.

4. The method for using a consumable medical product according to claim 1, further comprising adding new information at the vendor site for reuse of the product.

5. The method for using a consumable medical product according to claim 1, wherein the retrieved information is used in billing the consumer site.

6. A method of using a consumable medical product including transferring information concerning the consumable medical product comprising the steps of:

a) receiving the consumable medical product having an associated record member at a vendor site;

b) writing information to the record member at the vendor site; and
c) retrieving the stored information at a consumer site for determining at least one operating parameter for a system for using the consumable medical product;

wherein said at least one operating parameter is at least one member selected from the group consisting of setting at least one pressure limit for the system, determining a volume of the system, removing air from the system, calibrating a pumping mechanism and preventing use of fluids beyond an expiration date.

7. The method of claim 6, wherein the product is a medical fluid delivery element.

8. A method for using a consumable medical product including transferring product information concerning said consumable medical product comprising the steps of:
 a) storing information on a record member associated with the consumable medical product at a vendor site;
 b) retrieving the stored information at a consumer site;
 c) calculating operating parameters for using the consumable medical product system based on the retrieved information;
 d) returning new information to the vendor site from the system via electromagnetic transmission.

* * * * *